United States Patent [19]

Morita et al.

[11] Patent Number: 4,992,530

[45] Date of Patent: Feb. 12, 1991

[54] CALCITONIN-GENE-RELATED PEPTIDE DERIVATIVES

[75] Inventors: Kaoru Morita; Toyonobu Uzawa; Masayuki Hori; Toshiharu Noda, all of Shizuoka, Japan

[73] Assignee: Toyo Jozo Kabushiki Kaisha, Shizuoka, Japan

[21] Appl. No.: 222,761

[22] Filed: Jul. 21, 1988

[30] Foreign Application Priority Data

Jul. 22, 1987 [JP] Japan .................. 62-182891

[51] Int. Cl.$^5$ .................. C07K 5/00; A61K 37/02
[52] U.S. Cl. .................................. 530/307
[58] Field of Search .......................... 530/307

[56] References Cited

U.S. PATENT DOCUMENTS 4,743,677  5/1988  Noda et al. .................. 530/307

FOREIGN PATENT DOCUMENTS 0212432  3/1987  European Pat. Off. .

OTHER PUBLICATIONS

"Isolation and Partial Characterization of the Calcitonin Gene in a Lower Vertebrate", FEBS, vol. 203, No. 1, Jul. 1986, by S. Minvielle et al., pp. 7-10.
"Isolation and Characterization of Human Celcitonin Gene-Related Peptide", Nature, vol. 308, No. 19, Apr. 1984, by H. Morris et al., pp. 746-748.
"A Second Human Calcitonin/CGRP Gene", Federation of European Biochemical Societies, vol. 183, No. 2, Apr. 1985, by P. Steenbergh et al., pp. 403-407.
"The Myotropic and Plasma-Calcium Modulating Effects of Calcitonin Gene-Related Peptide", Neuropeptides, vol. 4, Part 5, 1984, by J. Tippins et al., pp. 425-434.
"Calcitonin Gene-Related Peptide is a Potent Vasodilator", Nature, vol. 313, No. 3, Jan. 1985, by S. Brain et al., pp. 54-56.

Primary Examiner—Mary C. Lee
Assistant Examiner—J. Richter
Attorney, Agent, or Firm—Young & Thompson

[57] ABSTRACT

A compound of the formula

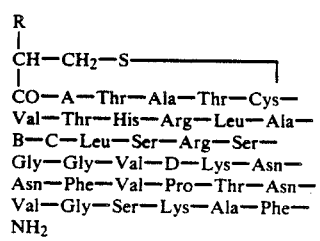

wherein R is H or H-Ala-NH- and when A is Asp, B is Asp or Glu, C is Leu and D is Val; when A is Asn and B is Gly, C is Phe and D is Gly; when A is Asn, B is Asp or Glu and C is Leu, D is Gly; and when A is Asn, B is Asp or Glu, and C is Phe, D is Val, or a pharmaceutically acceptable salt thereof, is useful for the treatment of calcium metabolic disorders, cardiac disease and ulcers, and for the improvement of cerebral circulation.

1 Claim, 2 Drawing Sheets

CALCITONIN-GENE-RELATED PEPTIDE DERIVATIVES

FIELD OF THE INVENTION

This invention relates to novel human calcitonin-gene-related peptide (hereinafter designated as h-CGRP) derivatives, useful for the treatment of calcium metabolic disorders, cardiac disease and ulcers, and for the improvement of cerebral circulation.

THE KNOWN PRIOR ART h-CGRP has an amino acid sequence of the formula

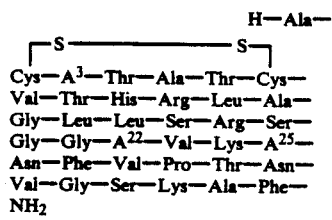

wherein $A^3$ is Asp or Asn, $A^{22}$ is Val or Met, and $A^{25}$ is Asn or Ser, and is known to have various biological properties [Nature, 308(19): 746–748 (1984), FEBS Letters, 183(2): 403 (1985), Neuropeptides, 4: 425–434 (1984) and Nature, 313(3): 54–56].

OBJECTS OF THE INVENTION

An object of the present invention is to provide novel h-CGRP derivatives.

Another object of the invention is to synthesize h-CGRP derivatives having properties superior to those of h-CGRP, especially superior properties in terms of serum calcium and phosphate reducing activities.

SUMMARY OF THE INVENTION

We have synthesized various derivatives of h-CGRP and have made comparative studies of their biological activities. As a result, we have found that they have stronger serum calcium reducing activity and serum phosphate reducing activity with prolonged action, as compared with known h-CGRP.

More particularly, the present invention provides novel h-CGRP derivatives of the formula

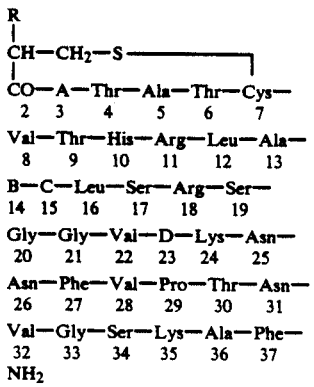

wherein R is H or H—Ala—NH— and when A is Asp, B is Asp or Glu, C is Leu and D is Val; when A is Asn and B is Gly, C is Phe and D is Gly; when A is Asn, B is Asp or Glu and C is Leu, D is Gly; and when A is Asn, B is Asp or Glu, and C is Phe, D is Val, or a pharmaceutically acceptable salt thereof.

A peptide (1) of the present invention can be synthesized by a known conventional process for peptide synthesis, e.g. a process by liquid phase synthesis as follows:

When R is H, a peptide (1) is synthesized by converting a carboxyl in phenylalanyl in the C-terminal to an amide, condensing successively a protected amino acid and/or a protected lower peptide in the order of amino acid sequence as shown in the formula (1), when R is H, removing the protective group for L-cysteinyl and mercapto in the β-mercaptopropionyl group and the protective group for the functional group in the other side chain by acid hydrolysis, and when R is H—Ala—NH—, removing the protective group for mercapto in L-cysteinyl and the protective group for the functional group in the other side chain by acid hydrolysis, and oxidizing L-cysteinyl (or the β-mercaptopropionyl group) and mercapto in L-cysteinyl to form a disulfide bridge at a final stage of the condensation reaction.

The condensation reaction can be effected by repeating the removal and addition of a protective group and the condensation reaction according to the process for conventional peptide synthesis. A protective group for a starting material and intermediates used in the process for the production of a peptide (1) of the present invention is a known protective group in peptide chemistry, for example a protective group which can be easily removed by a known procedure such as hydrolysis, acid decomposition, reduction, aminolysis or hydrazinolysis. The protective groups are well known in the literature of peptide chemistry.

Examples of preferred protective groups are butyloxy carbonyl, benzyloxy carbonyl or p-methoxybenzyloxy carbonyl for an α-amino group, benzyloxy carbonyl or p-chlorobenzyloxy carbonyl for a side chain amino group such as the ε-amino group in lysine, a methyl ester or benzyl ester for an α-carboxyl group, a benzyl ester for a side chain carboxyl group such as the side chain carboxyl in aspartic acid or glutamic acid, benzyl for a hydroxyl group in serine or threonine, mesitylene-2-sulfonyl or tosyl for the amino group of guanidino in arginine and p-methoxybenzyl or acetamididomethyl for the mercapto group of cysteine or β-mercaptopropionic acid.

In the synthesis of a peptide (1) of the present invention, the condensation of each amino acid and/or lower peptide can be effected by reacting an amino acid or a lower peptide having protected α-amino and activated terminal α-carboxyl, with an amino acid or a lower peptide having free α-amino and a protected terminal carboxyl group, or alternatively by reacting an amino acid or a lower peptide having activated α-amino and protected terminal carboxyl with an amino acid or a lower peptide having a protected α-amino and a free terminal carboxyl group.

A carboxyl group can be activated by conversion, for example to acid azide, acid anhydride, acid imidazolide or an activated ester such as cyanomethyl ester, p-nitrophenyl ester or N-hydroxysuccinimide ester. Furthermore, it can be activated by using a condensation reagent, for example a carbodiimide such as N,N'-dicyclohexyl-carbodiimide (DCC), N-ethyl-N'-3-dimethylaminopropyl-carbodiimide or N,N'-carbonyldiimidazole.

Examples of preferred condensation reactions used in the present invention are the azide method, the activated ester method, the mixed anhydride method and the carbodiimide method. In the condensation reaction, it is preferred to avoid or at least to minimize the racemization reaction; and preferred such processes are the azide method, the activated ester method, the Wunsch method [Z. Naturforsch., 21b, 426 (1966)] or the Geiger method [Chem. Ber., 103, 788 (1970)].

The peptide (1) can be synthesized by any procedure; however, it is preferable to construct an amino acid sequence by connecting amino acid and/or lower peptide in order from the C-terminal.

A peptide (1) wherein R is H can be obtained by removing the protective groups in the protected peptide chain, namely β-mercaptopropionyl pentatriaconta-peptideamide having protected ε-amino, side chain carboxyl, hydroxyl, guanidino and mercapto groups. These protective groups are preferably removed by one-step removal by acid hydrolysis using for example trifluoro-methane sulfonic acid or anhydrous hydrogen fluoride to obtain β-mercaptopropionyl pentatriaconta-peptideamide having a free mercapto group.

A peptide (1) where R is H—Ala—NH— can be obtained by removing the protective groups in the protected peptide chain, namely heptatriaconta-peptideamide having protected ε-amino, side chain carboxyl, hydroxyl, guanidino and mercapto groups. These protective groups are preferably removed in the same way as above to obtain heptatriaconta-peptideamide having a free mercapto group.

In the said peptide-amide, an inner molecular disulfide linkage is formed by oxidation to obtain the peptide (1). Disulfide linkage can be effected generally by oxidation with oxygen in water, diiodo-ethane in an organic solvent, iodine in glacial acetic acid or potassium ferricyanide in water.

A process by solid phase synthesis is as follows:

A solid phase peptide synthesis method can be used in part or in whole as the process of peptide (1) synthesis. For example, in the case of the synthesis of peptide (1), a peptide fragment (3-37) [hereinafter the peptide of amino acid sequence constituted by amino acids from Nos. 3 to 37 is abbreviated as peptide fragment (3-37) or peptide (3-37)] is synthesized by a solid phase method, and the α-amino group in the said peptide is acylated with β-mercaptopropionic acid to obtain a protected pentatriaconta-peptide-bound resin or a protected heptatriaconta-peptide-bound resin. These protective groups and the resin are removed by a known method such as using trifluoromethane sulfonic acid or anhydrous hydrogen fluoride in a one-step removal to obtain a β-mercaptopropionyl pentatriaconta-peptideamide having a free mercapto group or a heptatriaconta-peptideamide having a free mercapto group. A peptide (1) can be obtained by constructing an inner molecule disulfide bond as set forth in the process by liquid phase synthesis hereinabove.

Examples of resins used in the solid phase method are conventional resins such as benzhydrylamine resin or p-methyl-benzhydrylamine resin. A resin with the desired functional equivalent or cross-linkage can be synthesized but is also commercially available.

In the solid phase method, an amino acid is condensed in the resin, in the order of the amino acid sequence of formula (I), from the C-terminal amino acid to the third amino acid (amino acid No. 3) or from the C-terminal amino acid to the first amino acid (amino acid No. 1), and in the case of a peptide wherein R is H, it is acylated with β-mercaptopropionic acid upon the condensation to the third amino acid. A functional group in the amino acid is protected by a known method. Examples of protective groups are set forth hereinbefore.

In the solid phase reaction, a resin in a reaction vessel is swelled by adding dichloromethane, chloroform, dimethylformamide, benzene or a solvent for swelling the resin, in a ratio of 2-20 ml solvent per 1 g resin. In another reaction vessel, 1-6 equivalents of t-butyloxycarbonyl (hereinafter designed Boc-) amino acid per 1 equivalent of amino group in the resin are first reacted with DCC, and the obtained acid anhydride, which is separated from a by-product dicyclohexylurea (hereinafter designed DCU), is added to the resin hereinabove. The amount of condensation agent (DCC) is 0.5-3 equivalents per 1 equivalent of Boc-amino acid. The reaction proceeds generally for 5-60 minutes.

The coupling amount of amino acid or peptide can be determined according to a conventional method [T. Fairwell et al., Biochemistry, 22: 2691 (1983)] by checking the amount of Boc-amino acid upon sampling the Boc-amino acid-resin or Boc-peptide-resin obtained in each process.

The protective group for the o-amino group, Boc, is removed by an acid such as trifluoroacetic acid and the condensation reaction is performed. An automatic solid phase synthesizer can be used; however, a manual procedure can also be used. The entire operation is preferably performed under a nitrogen gas atmosphere.

In this way, a peptide fragment (3-37) or (1-37) bound to a resin can be obtained.

A peptide fragment (3-37) bound to resin is acylated with β-mercaptopropionic acid in the final step to obtain a β-mercaptopropionyl-protected pentatriaconta peptide amide-bound resin.

The thus-obtained protected pentatriaconta peptide amide-bound resin or protected heptatriaconta peptide amide-bound resin is, as previously described, treated with anhydrous hydrogen fluoride to remove the protective group and resin in one-step, whereby β-mercaptopropionyl pentatriaconta peptide-amide having a free mercapto group or heptatriaconta peptide-amide having a free mercapto group can be obtained.

A peptide (1) can be obtained by forming intramolecular disulfide bonds in the above peptide-amide. Isolation and purification:

The thus-obtained peptide (1) can be purified by purification methods which are well known in peptide or protein chemistry. For example, a gel-filtration method can be carried out using Sephadex G-25, Sephadex G-50 or Sephadex LH-20 (trade names), or ion-exchange chromatography using carboxy methyl cellulose, or another resin, or HPLC can be used.

Examples of a peptide (1) of the present invention are illustrated as follows:

[Asn$^3$, Phe$^{15}$, Gly$^{23}$] h-CGRP (1-37);
  R = H—Ala—NH—, A = Asn,
  B = Gly, C = Phe, D = Gly
desalanyl-deamino- [Asn$^3$, Phe$^{15}$, Gly$^{23}$] h-CGRP (2-37);
  R = H, A = Asn, B = Gly,
  C = Phe, D = Gly,
[Asn$^3$, Asp$^{14}$, Gly$^{23}$] h-CGRP (1-37);
  R = H—Ala—NH—, A = Asn,
  B = Asp, C = Leu, D = Gly
desalanyl-deamino- [Asn$^3$, Asp$^{14}$, Gly$^{23}$] h-CGRP (2-37);
  R = H, A = Asn, B = Asp,
  C = Leu, D = Gly,
[Asn$^3$, Asp$^{14}$, Phe$^{15}$] h-CGRP (1-37);
  R = H—Ala—NH—, A = Asn,
  B = Asp, C = Phe, D = Val -continued desalanyl-deamino- [Asn³, Asp¹⁴, Phe¹⁵] h-CCGRP (2-37);
  R = H, A = Asn, B = Asp, C = Phe, D = Val
[Asp¹⁴] h-CGRP (1-37);
  R = H—Ala—NH—, A = Asp,
  B = Asp, C = Leu, D = Val
desalanyl-deamino- [Asp¹⁴] h-CGRP (2-37);
  R = H, A = Asp, B = Asp,
  C = Leu, D = Val
[Asn³, Glu¹⁴, Gly²³] h-CGRP (1-37);
  R = H—Ala—NH—, A = Asn,
  B = Glu, C = Leu, D = Gly
desalanyl-deamino- [Asn³, Glu¹⁴, Gly²³] h-CGRP (2-37);
  R = H, A = Asn, B = Glu,
  C = Leu, D = Gly,
[Asn³, Glu¹⁴, Phe¹⁵] h-CGRP (1-37);
  R = H—Ala—NH—, A = Asn,
  B = Glu, C = Phe, D = Val
desalanyl-deamino- [Asn³, Glu¹⁴, Phe¹⁵] h-CGRP (2-37);
  R = H, A = Asn, B = Glu,
  C = Phe, D = Val
[Glu¹⁴] h-CGRP (1-37);
  R = H—Ala—NH—, A = Asp,
  B = Glu, C = Leu, D = Val
desalanyl-deamino- [Glu¹⁴], h-CGRP (2-37);
  R = H, A = Asp, B = Glu,
  C = Leu, D = Val A peptide (1) of the present invention can be obtained according to the process in the form of a free base or salt. For example, a salt of a known organic acid such as acetic acid, citric acid, malic acid or tartaric acid can be prepared.

The abbreviations in the specification are identified as follows:

| | |
|---|---|
| Ala | L-alanine |
| Asp | L-aspartic acid |
| Glu | L-glutamic acid |
| Asn | L-asparagine |
| Thr | L-threonine |
| Cys | L-cysteine |
| Val | L-valine |
| His | L-histidine |
| Arg | L-arginine |
| Leu | L-leucine |
| Gly | glycine |
| Phe | L-phenylalanine |
| Ser | L-serine |
| Lys | L-lysine |
| Pro | L-proline |
| Met | L-methionine |
| Boc | t-butyloxycarbonyl |
| Cl-Z | p-chlorobenzyloxycarbonyl |
| Bzl | benzyl |
| MBzl | p-methoxybenzyl |
| Tos | tosyl |
| OBzl | benzyl ester |
| TFA | trifluoroacetic acid |
| DMF | N,N'-dimethylformamide |
| DCM | dichloromethane |
| DCC | N,N'-dicyclohexylcarbodiimide |
| DIEA | diisopropylethylamine |
| HOBt | 1-hydroxybenzotriazole |
| MBHA-resin | p-methylbenzhydrylamine resin |

UTILITY OF THE INVENTION

Serum calcium and serum phosphate reducing activities: Assay method:

The peptide (1) of the present invention and known h-CGRP (each 80 μg) dissolved in citrate buffer, pH 6.5, containing 0.1% bovine serum albumin (hereinafter designated dissolving medium) (1 ml) were administered intravenously into the tail vein of Wistar rats, body weight 80-90 g, 5-6 rats in one group, at 80 μg/kg. After 30 and 60 mins. of administration, blood samples were collected from the abdominal descending aorta. The serum calcium concentration was measured by atomic adsorption spectrophotometry. Serum phosphate was measured by a method according to Goldenberg et al. [Clin. Chem., 12: 872-882 (1966)].

RESULTS

Figure 1:
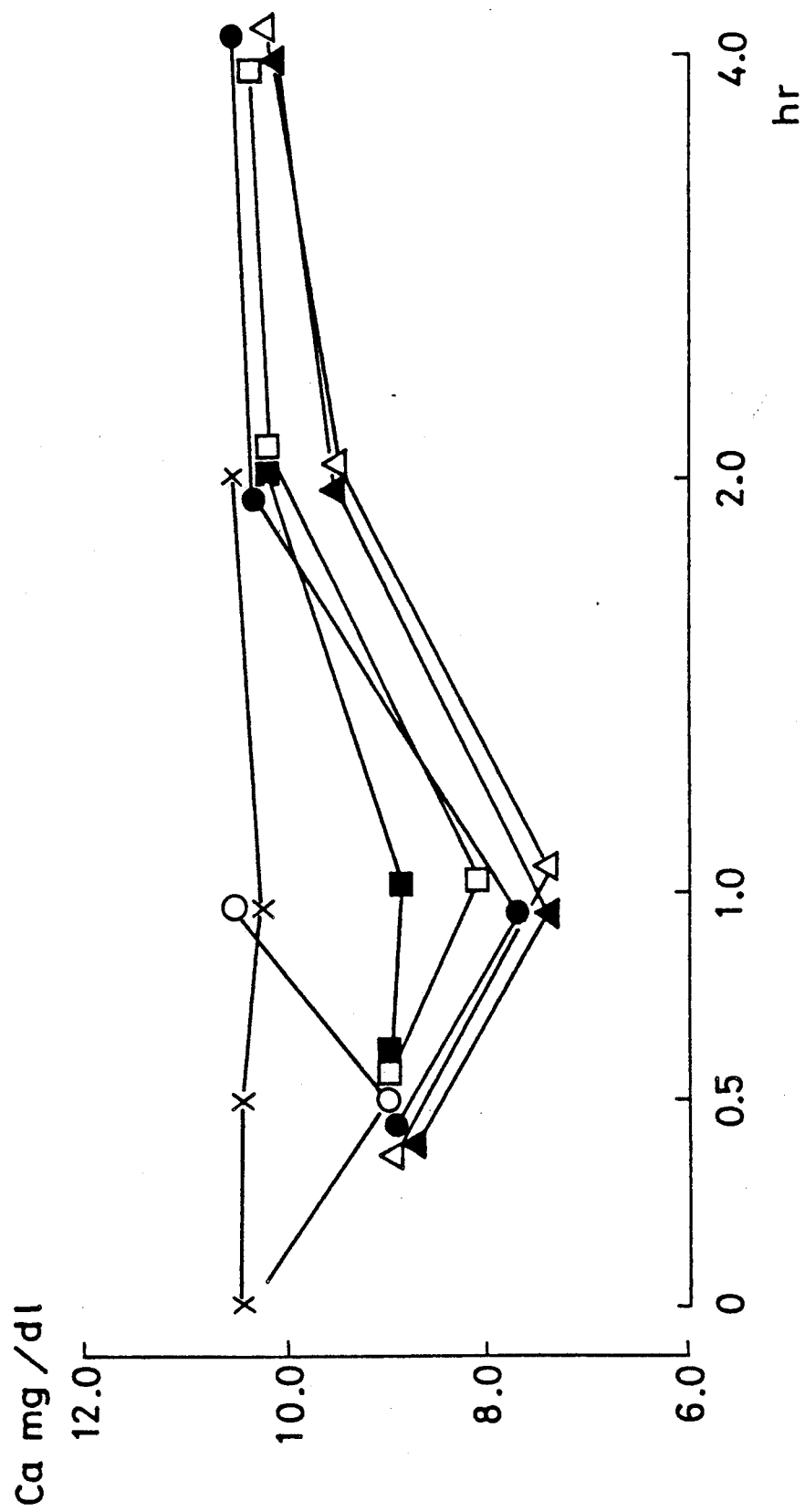
FIG. 1 is a graph showing the rat serum calcium reducing effect of h-CGRP and peptide (1) of the present invention.
Figure 2:
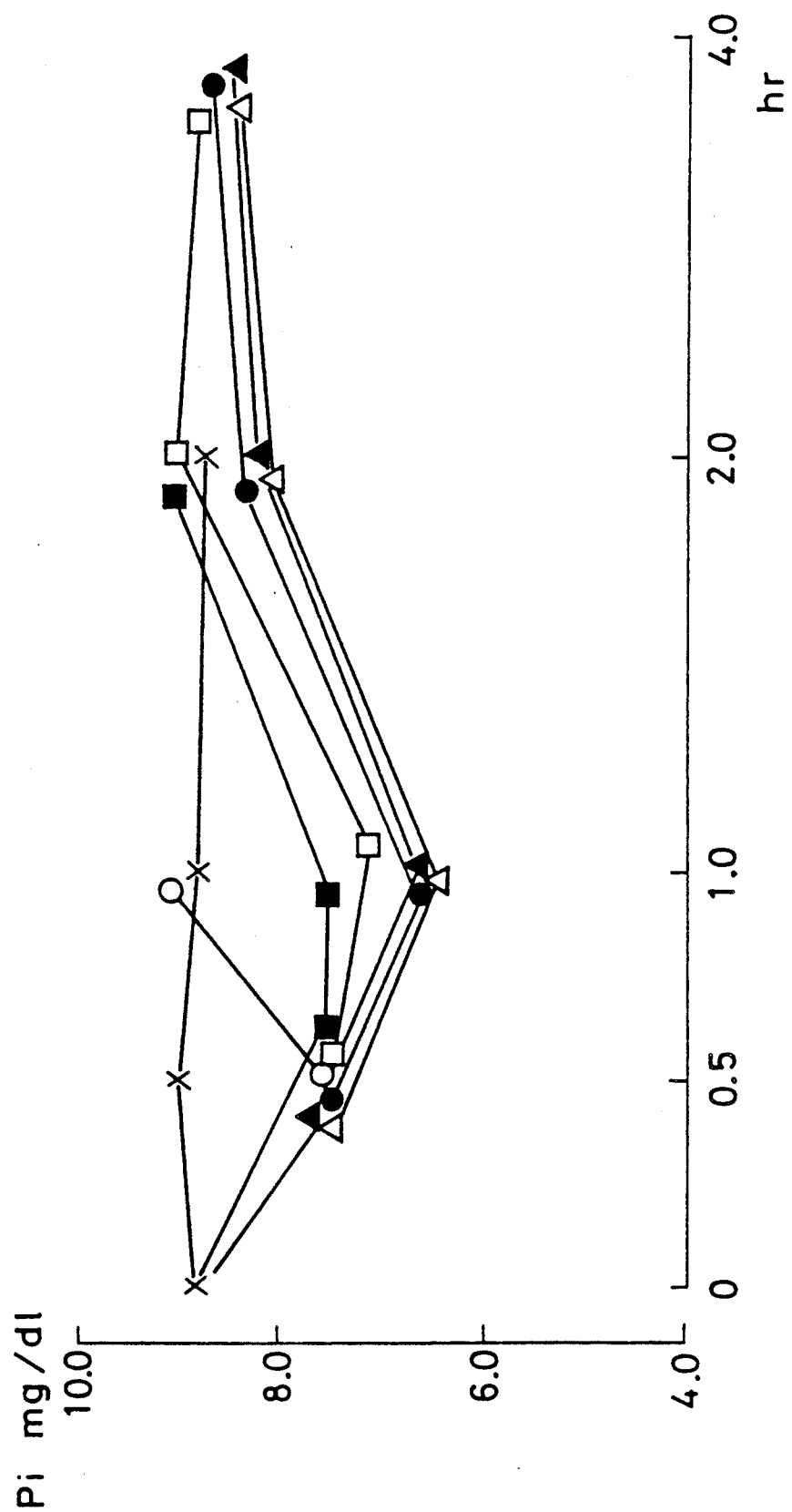
FIG. 2 is a graph showing the rat serum inorganic phosphate reducing effect of h-CGRP and peptide (1) of the present invention.

As shown in FIGS. 1 and 2, the concentrations of serum calcium and phosphate were reduced by more than 20-30% in the desalanyl-deamino-[Asp14] h-CGRP(2-37), 80 μg/kg, administered group [-●-], [Asp¹⁴] h-CGRP(1-37) [-□-], [Asn³, Phe¹⁵,Gly²³] h-CGRP(1-37) [-■-], [Asn³,Asp¹⁴,Gly²³] h-CGRP(1-37) [-Δ-], and Asn³,Asp¹⁴,Phe¹⁵] h-CGRP(1-37) ]-▲-] as compared with the control group (dissolved medium administered group) [-X-] and these activities were observed to continue more than 2 hours. These activities were stronger than those of h-CGRP [-O-] and the effects were prolonged significantly.

As illustrated hereinabove, the peptide (1) of the present invention has stronger serum calcium reducing activity and serum phosphate reducing activity than known h-CGRP. Furthermore, it has longer-lasting activity than known h-CGRP. Moreover, it is useful for the treatment of calcium metabolic disorders, cardiac disease and ulcer,s or for the improvement of cerebral circulation.

The following examples illustrate the present invention.

EXAMPLE 1

Production of [Asn³,Phe¹⁵,Gly²³] h-CGRP(1-37):

Anisole (2 ml), dimethylsulfide (2 ml) and ethanedithiol (0.4 ml) were added to [Asn³,Phe¹⁵,Gly²³] h-CGRP(1-37)-MBHA-resin of the formula

| |
|---|
| [Asn³, Phe¹⁵, Gly²³] h-CGRP (1-37) |
| H—Ala—Cys (MBzl)—Asn—Thr (Bzl) |
| —Ala—Thr (Bzl)—Cys (MBzl)—Val— |
| Thr (Bzl)—His (Tos)—Arg (Tos)— |
| Leu—Ala—Gly—Phe—Leu—Ser (Bzl) |
| —Arg (Tos)—Ser (Bzl)—Gly—Gly— |
| Val—Gly—Lys (Cl—Z)—Asn—Asn— |
| Phe—Val—Pro—Thr (Bzl)—Asn—Val |
| —Gly—Ser (Bzl)—Lys (Cl—Z)—Ala |
| —Phe—MBHA—resin |

(1.09 g). Anhydrous hydrogen fluoride (20 ml) was added thereto and the mixture was stirred at 0° C. for 1 hour. After the anhydrous hydrogen fluoride was distilled off in vacuo, the residue was washed with ether and 20% acetic acid (30 ml) was added thereto to extract the peptide. The extract was passed through a Dowex WGR (trademark) column (2.5×15 cm) and eluted with 1M acetic acid (150 ml). The eluate was freeze dried to obtain a white powder (400 mg). This powder (200 mg) was dissolved in 50 mM Na₂HPO₄ buffer (pH 7.5, 15 ml) containing 8M urea and 5 mM dithiothreitol, and the mixture was stirred for 1 hour, then diluted with 50 mM Na₂HPO₄ buffer (pH 7.5, 1300 ml), and thereafter 20 mM K₃Fe(CN)₆ aqueous solution (9 ml) was added thereto. The solution was charged on a column of CHP-20P (Mitsubishi Kasei Kogyo trade name) (2.5×10 cm) and was subjected to linear gradient elution with 0.1N aqueous formic acid (600 ml) containing 5% acetonitrile - 0.1N aqueous formic acid (600 ml) containing 45% acetonitrile. Samples (100 μl) from the fractions (each 10 ml) were measured colorimetrically by the Folin-Lolly method at 750 nm. Fractions Nos. 44-65 were collected and lyophilized to obtain a white powder (60 mg). The residual powder (200 mg) was treated in the same way to obtain a further white powder (60 mg). The combined powder was charged on a column (2.5×15 cm) of CM-Toyopearl 650M (trademark), and eluted by linear gradient elution with 0.1N aq. acetic acid (700 ml) - 0.4M aq. ammonium acetate (pH 5, 700 ml). Fractions (each 10 ml) Nos. 105-123 were collected and freeze dried to obtain a white powder. The thus-obtained white powder dissolved in 0.1M acetic acid was charged on a column of Sephadex G-25 Fine (trade name) (2.6×90 cm) and eluted with 0.1M acetic acid. Fractions Nos. 23-36 (each 10 ml) were collected and lyophilized to obtain a white powder (42.8 mg). This powder was purified by reverse-phase HPLC to obtain purified [Asn³Phe¹⁵,Gly²³] h-CGRP(1-37) (20.3 mg).

| Column | Nucleosil 5C₁₈ (8 mm ID × 250 mm) |
|---|---|
| Buffer | 0.1% TFA-acetonitrile (a gradient solution with acetonitrile concentration from 28 to 32% for 20 minutes) |
| Flow | 2.5 ml/min. |
| Fraction | collected at a peak at retention time 16.3 min. |

Physical properties:

$[\alpha]_D^{26.5}: -56.63°$ (c=0.113, 0.1M acetic acid)

Amino acid analysis (6N-HCl hydrolysis):

| Asp 3.86 (4), Thr 3.82 (4), |
|---|
| Ser 2.90 (3), Pro 1.28 (1), |
| Gly 4.97 (5), Ala 4.00 (4), |
| Val 4.10 (4), Leu 2.05 (2), |
| Phe 2.95 (3), Lys 2.07 (2), |
| His 0.98 (1), Arg 1.92 (2), |
| Cystine 0.50 (1) |

Amino acid analysis (enzymatic hydrolysis by trypsin-amino-peptidase M):

| Asn 3.78 (4), Thr 3.86 (4), |
|---|
| Ser 3.13 (3), Pro 0.97 (1), |
| Gly 4.95 (5), Ala 4.00 (4), |
| Val 4.19 (4), Leu 2.19 (2), |
| Phe 2.92 (3), Lys 2.19 (2), |
| His 0.92 (1), Arg 1.92 (2), |
| Cystine 0.87 (1) |

Arg is analyzed by citrulline.

The above protected [Asn³,Phe¹⁵,Gly²³] h-CGRP(1-37)-MBHA-resin was obtained by the following procedure:

Solid phase peptide synthesizer: 430-A peptide synthesizer Applied Biosystems Inc.

MBHA-resin (Applied Biosystems Inc., amino group: 0.48 mM/g) (1.04 g) in a reaction vessel for solid-phase peptide synthesis was treated with DCM (8 ml) (4 times, each 1 min.), DCM solution (8 ml) containing 60% TFA (20 min.), DCM (4 ml) (3 times, each 15 sec.), DMF solution (3 ml) containing DIEA (1 ml) (2 times, each 1 min.) and DMF (8 ml) (6 times, each 40 sec.), in this order, under a nitrogen gas atmosphere with stirring. The material was filtered after each treatment.

DCC (0.5M-DCM solution) (2 ml) was added to Boc-Phe (2 mM, amino acid sequence No. 37) dissolved in DCM (5 ml) in a vessel for amino acid activation and reacted for 5 mins. The filtered reaction mixture was transferred to a vessel for concentration, and DMF (3 ml) was added therein, then DCM was distilled off under a nitrogen gas atmosphere. Further DMF (3 ml) was added, and the mixture was transferred to the above reaction vessel, then reacted for 25 mins. The reaction mixture was washed six times with DCM (8 ml), 20 sec. each time, and the mixture was filtered to obtain Boc-Phe-MBHA-resin.

Boc-Phe-MBHA-resin hereinabove was washed four times with DCM (8 ml, each 1 min.) in the reaction vessel and filtered. 40% DCM solution (8 ml) containing 60% TFA was added thereto and the mixture was stirred for 20 min. to remove Boc. The thus-obtained resin was washed three times with DCM (4 ml, each 15 sec.), two times with DMF solution (3 ml) containing DIEA (1 ml) (each 1 min.) and six times with DMF (8 ml, each 40 sec.), in this order, and filtered.

DCC (0.5M-DCM solution) (2 ml) was added to Boc-Ala (2 mM, amino acid sequence No. 36) dissolved in DCM (5 ml) in a vessel for amino acid activation and reacted for 5 mins., then treated the same as Boc-Phe hereinabove. The reaction mixture was concentrated after adding DMF under a nitrogen gas atmosphere, transferred into a reaction vessel and reacted for 20 mins. washed six times with DCM (8 ml, each 20 sec.) and filtered to obtain Boc-Ala-Phe-MBHA-resin.

Subsequently, amino acids (sequence from Nos. 1 to 35) were subjected to a coupling reaction and at a final step of the reaction Boc was removed by DCM solution containing 60% TFA, then washed with DCM, DIEA and DMF to obtain protected [Asn³,Phe¹⁵,Gly²³] h-CGRP(1-37)-MBHA-resin.

The protected amino acids used in the process are as follows:

| Amino Acid No. | Protected Amino Acid | Amount Used (mM) |
|---|---|---|
| 37 | Boc—Phe | 2 |
| 36 | Boc—Ala | 2 |
| 35 | Boc—Lys (Cl—Z) | 2 |
| 34 | Boc—Ser (Bzl) | 2 |
| 33 | Boc—Gly | 2 |
| 32 | Boc—Val | 2 |
| 31 | Boc—Asn | 2 × 2 |
| 30 | Boc—Thr | 2 |
| 29 | Boc—Pro | 2 |
| 28 | Boc—Val | 2 |
| 27 | Boc—Phe | 2 |
| 26 | Boc—Asn | 2 × 2 |
| 25 | Boc—Asn | 2 × 2 |
| 24 | Boc—Lys (Cl—Z) | 2 |
| 23 | Boc—Gly | 2 |
| 22 | Boc—Val | 2 |
| 21 | Boc—Gly | 2 |
| 20 | Boc—Gly | 2 |
| 19 | Boc—Ser (Bzl) | 2 |
| 18 | Boc—Arg (Tos) | 2 × 2 |
| 17 | Boc—Ser (Bzl) | 2 |
| 16 | Boc—Leu | 2 |
| 15 | Boc—Phe | 2 |
| 14 | Boc—Gly | 2 |
| 13 | Boc—Ala | 2 |

| Amino Acid No. | Protected Amino Acid | Amount Used (mM) |
|---|---|---|
| 12 | Boc—Leu | 2 |
| 11 | Boc—Arg (Tos) | 2 × 2 |
| 10 | Boc—His (Tos) | 2 |
| 9 | Boc—Thr (Bzl) | 2 |
| 8 | Boc—Val | 2 |
| 7 | Boc—Cys (MBzl) | 2 |
| 6 | Boc—Thr (Bzl) | 2 |
| 5 | Boc—Ala | 2 |
| 4 | Boc—Thr (Bzl) | 2 |
| 3 | Boc—Asn | 2 × 2 |
| 2 | Boc—Cys (MBzl) | 2 |
| 1 | Boc—Ala | 2 |

In the above solid phase synthesis, when Asn and Arg were used, DCC solution (3 ml) and HOBt solution (0.5M-DMF solution) (4 ml) were added to the amino acids (2 mM). The mixture was reacted for 35 min., then treated the same as the other amino acids. The mixture was transferred into a reaction vessel for the coupling reaction, washed with DCM and filtered. Further DCC solution (3 ml) and HOBt solution (0.5M-DMF solution) (4 ml) were added again to the amino acids (2 mM), the mixture was reacted for 35 mins., and then the mixture was transferred into a reaction vessel for the coupling reaction according to the so-called double coupling method.

EXAMPLE 2

Production of [$Asn^3, Asp^{14}, Gly^{23}$] h-CGRP(1–37):

Anisole (2 ml), dimethylsulfide (2 ml) and ethanedithiol (0.4 ml) were added to [$Asn^3, Asp^{14}, Gly^{23}$] h-CGRP(1–37)-MBHA-resin of the formula

```
H—Ala—Cys (MBzl)—Asn—Thr
(Bzl)—Ala—Thr (Bzl)—Cys (MBzl)
—Val—Thr (Bzl)—His (Tos)—Arg
(Tos)—Leu—Ala—Asp (OBzl)—Leu—
Leu—Ser (Bzl)—Arg (Tos)—Ser
(Bzl)—Gly—Gly—Val—Gly—Lys
(Cl—Z)—Asn—Asn—Phe—Val—Pro—
Thr (Bzl)—Asn—Val—Gly—Ser
(Bzl)—Lys (Cl—Z)—Ala—Phe—MBHA
—resin
```

(1.173 g). Anhydrous hydrogen fluoride (20 ml) was added thereto and the mixture was stirred at 0° C. for 1 hour. After the anhydrous hydrogen fluoride was distilled off in vacuo, the residue was washed with ether and 20% acetic acid (30 ml) was added thereto to extract the peptide. The extract was passed through the Dowex WGR (trademark) column (2.5×15 cm) and eluted with 0.1M acetic acid (150 ml). The eluate was freeze dried to obtain a white powder (460 mg).

This powder dissolved in 01.M acetic acid was charged on a column (3.0×90 cm) of Sephadex G-25 Fine and eluted with 0.1M acetic acid. The eluate was separated at each 10 ml fraction. Fractions Nos. 28–40 were collected and lyophilized to obtain a white powder (306.6 mg). This powder (152 mg) was dissolved in 50 mM Na₂HPO₄ buffer (pH 7.5, 10 ml) containing 8M urea and 5 mM dithiothreitol, and the mixture was stirred for 1 hour, then diluted with 50 mM Na₂HPO₄ buffer (pH 7.5, 1125 ml), thereafter 20 mM K₃Fe(CN)₆ aqueous solution (8 ml) was added thereto. The solution was charged on a column of CHP-20P (Mitsubishi Kasei Kogyo trade name) (2.5×14 cm) and was subjected to linear gradient elution with 0.1N aqueous formate (500 ml) containing 5% acetonitrile - 0.1N aqueous formate (500 ml) containing 45% acetonitrile.

Samples (100 μl) from the fractions (each 10 ml) were measured colorimetrically by the Folin-Lolly method at 750 nm. Fractions Nos. 41-55 were collected and lyophilized to obtain a white powder (60 mg). The residual powder (154 mg) was treated by the same way to obtain further white powder (40 mg). The combined powder was charged on a column (2.5×20 cm) of CM-Toyopearl 650M (trademark), and eluted by linear gradient elution with distilled water (700 ml)-0.4M aq. ammonium acetate (pH 5, 700 ml). Fractions (each 10 ml) Nos. 108-116 were collected and freeze dried to obtain a white powder. The thus-obtained white powder dissolved in 0.1M acetic acid was charged on a column of Sephadex G-25 Fine (trade name) (2.6×90 cm) and eluted wit 0.1M acetic acid. Fractions Nos. 8-14 (each 10 ml) were collected and lyophilized to obtain a white powder (13.0 mg). This powder was purified by reverse phase HPLC to obtain purified [$Asn^3, Asp^{14}, Gly^{23}$] h-CGRP(1-37) (4.7 mg).

| | |
|---|---|
| Column | Nucleosil $5C^{18}$ (8 mm ID × 250 mm) |
| Buffer | 0.1% TFA-acetonitrile (a gradient elution with acetonitrile concentration from 28 to 32% for 25 mins.) |
| Flow | 2.5 ml/min. |
| Fraction | collected at a peak at retention time 17.3 min. |

Physical properties:

$[\alpha]_D^{25}: -62.29°$ (c=0.122, 0.1M acetic acid)

Amino acid analysis (6N-HCl hydrolysis):

| |
|---|
| Asp 4.96 (5), Thr 3.70 (4), |
| Ser 2.73 (3), Pro 1.17 (1), |
| Gly 3.93 (4), Ala 4.00 (4), |
| Val 4.19 (4), Leu 3.12 (3), |
| Phe 2.01 (2), Lys 2.24 (2), |
| His 1.01 (1), Arg 1.95 (2), |
| Cystine 0.71 (1) |

Amino acid analysis (enzymatic hydrolysis by trypsin-amino-peptidase):

| |
|---|
| Asp 1.11 (1), Asn 3.46 (4), |
| Thr 3.86 (4), Ser 3.19 (3), |
| Pro 1.38 (1), Gly 4.01 (4), |
| Ala 4.00 (4), Val 14.26 (4), |
| Leu 3.23 (3), Phe 2.00 (2), |
| Lys 2.33 (2), His 0.95 (1), |
| Arg 1.89 (2), Cystine 0.88 (1) |

Arg is analyzed by citrulline.

The above protected [$Asn^3, Asp^{14}, Gly^{23}$] h-CGRP(1-37)-MBHA-resin was obtained in the same was as in Example 1.

The protected amino acids used in the process are as follows:

| Amino Acid No. | Protected Amino Acid | Amount Used (mM) |
|---|---|---|
| 37 | Boc—Phe | 2 |
| 36 | Boc—Ala | 2 |
| 35 | Boc—Lys (Cl—Z) | 2 |
| 34 | Boc—Ser (Bzl) | 2 |
| 33 | Boc—Gly | 2 |
| 32 | Boc—Val | 2 |

-continued

| Amino Acid No. | Protected Amino Acid | Amount Used (mM) |
|---|---|---|
| 31 | Boc—Asn | 2 × 2 |
| 30 | Boc—Thr | 2 |
| 29 | Boc—Pro | 2 |
| 28 | Boc—Val | 2 |
| 27 | Boc—Phe | 2 |
| 26 | Boc—Asn | 2 × 2 |
| 25 | Boc—Asn | 2 × 2 |
| 24 | Boc—Lys (Cl—Z) | 2 |
| 23 | Boc—Gly | 2 |
| 22 | Boc—Val | 2 |
| 21 | Boc—Gly | 2 |
| 20 | Boc—Gly | 2 |
| 19 | Boc—Ser (Bzl) | 2 |
| 18 | Boc—Arg (Tos) | 2 × 2 |
| 17 | Boc—Ser (Bzl) | 2 |
| 16 | Boc—Leu | 2 |
| 15 | Boc—Leu | 2 |
| 14 | Boc—Asp (OBzl) | 2 |
| 13 | Boc—Ala | 2 |
| 12 | Boc—Leu | 2 |
| 11 | Boc—Arg (Tos) | 2 × 2 |
| 10 | Boc—His (Tos) | 2 |
| 9 | Boc—Thr (Bzl) | 2 |
| 8 | Boc—Val | 2 |
| 7 | Boc—Cys (MBzl) | 2 |
| 6 | Boc—Thr (Bzl) | 2 |
| 5 | Boc—Ala | 2 |
| 4 | Boc—Thr (Bzl) | 2 |
| 3 | Boc—Asn | 2 × 2 |
| 2 | Boc—Cys (MBzl) | 2 |
| 1 | Boc—Ala | 2 |

EXAMPLE 3

Production of [Asn$^3$,Asp$^{14}$,Phe$^{15}$] h-CGRP(1-37):

Anisole (2 ml), dimethylsulfide (2 ml) and ethanedithiol (0.4 ml) were added to [Asn$^3$,Asp$^{14}$,Phe$^{15}$] h-CGRP(1-37)-MBHA-resin of the formula

```
H—Ala—Cys(MBzl)—Asn—Thr
(Bzl)—Ala—Thr(Bzl)—Cys(MBzl)—
Val—Thr(Bzl)—His(Tos)—Arg
(Tos)—Leu—Ala—Asp(OBzl)—Phe—
Leu—Ser(Bzl)—Arg(Tos)—Ser
(Bzl)—Gly—Gly—Val—Val—Lys
(Cl—Z)—Asn—Asn—Phe—Val—Pro—
Thr(Bzl)—Asn—Val—Gly—Ser
(Bzl)—Lys(Cl—Z)—Ala—Phe—MBHA—
resin
```

(1.173 g). Anhydrous hydrogen fluoride (20 ml) was added thereto and the mixture was stirred at 0° C. for 1 hour. After the anhydrous hydrogen fluoride was distilled off in vacuo, the residue was washed with ether and 20% acetic acid (30 ml) was added thereto to extract the peptide. The extract was passed through a Dowex WGR (trademark) column (2.5×15 cm) and eluted with 0.1M acetic acid (150 ml). The eluate was freeze dried to obtain a white powder (410 mg). This powder (150 mg) was dissolved in 50 mM Na$_2$HPO$_4$ buffer (pH 7.5, 10 ml) containing 8M urea and 5 mM dithiothreitol, and stirred for 1 hour at room temperature, then diluted with 50 mM Na$_2$HPO$_4$ buffer (pH 7.5, 1125 ml), thereafter 20 mM K$_3$Fe(CN)$_6$ aqueous solution (8 ml) was added thereto. The solution was charged on a column of CHP-20P (Mitsubishi Kasei Kogyo trade name) (2.5×12 cm) and was subjected to linear gradient elution with 0.1N aqueous formate (500 ml) containing 5% acetonitrile - 0.1N aqueous formate (500 ml) containing 45% acetonitrile. Samples (100 μl) from the fractions (each 10 ml) were measured colorimetrically by the Folin-Lolly method at 750 nm. Fractions Nos. 48-58 were collected and lyophilized to obtain a white powder (43 mg). The residual powder (260 mg) was treated in the same way to obtain further white powder (73 mg). The combined powder was charged on a column (2.5×10 cm) of CM-Toyopearl 650M (trademark), and eluted by linear gradient elution wit distilled water (500 ml) - 0.4 M aq. ammonium acetate (pH 5, 500 ml). Fractions Nos. 65-75 (each 10 ml) were collected and freeze dried to obtain a white powder. The thus-obtained white powder dissolved in 0.1M acetic acid was charged on a column of Sephadex G-25 Fine (trade name) (3×30 cm) and eluted with 0.1M acetic acid. Fractions Nos. 22-24 (each 10 ml) were collected and lyophilized to obtain a white powder (19.0 mg). This powder was purified by reverse phase HPLC to obtain purified [Asn$^3$, Asp$^{14}$,Phe$^{15}$] h-CGRP(1-37) (11 mg).

Column: Nucleosil 5C$_{18}$ (8 mm ID × 250 mm)
Buffer: 0.1% TFA-acetonitrile (a gradient elution with acetonitrile concentration from 30 to 33% for 20 mins.)
Flow: 2.5 ml/min.
Fraction: collected at a peak at retention time 12.9 min.

Physical properties:

$[\alpha]_D^{25}$: −63.68° (c=0.179, 0.1M acetic acid)

Amino acid analysis (6N-HCl hydrolysis):

Asp4.86(5), Thr3.81(4),
Ser2.89(3), Pro0.85(1),
Gly3.05(3), Ala4.00(4),
Val4.20(4), Leu2.13(2),
Phe3.01(3), Lys2.15(2),
His1.00(1), Arg2.03(2),
Cystine0.72(1)

Amino acid analysis (enzymatic hydrolysis by trypsin-amino-peptidase M):

Asp1.19(1), Asn3.64(4),
Thr3.93(4), Ser3.15(3),
Pro1.14(1), Gly3.15(3),
Ala4.00(4), Val5.02(5),
Leu2.25(2), Phe2.92(3),
Lys2.31(2), His1.01(1),
Arg2.00(2), cystine0.82(1)

Arg is analyzed by citrulline.

The above protected [Asn$^3$,Asp$^{14}$,Phe$^{15}$] h-CGRP(1-37)-MBHA-resin was obtained in the same way as in Example 1.

The protected amino acids used in the process are as follows:

| Amino Acid No. | Protected Amino Acid | Amount Used (mM) |
|---|---|---|
| 37 | Boc—Phe | 2 |
| 36 | Boc—Ala | 2 |
| 35 | Boc—Lys(Cl—Z) | 2 |
| 34 | Boc—Ser(Bzl) | 2 |
| 33 | Boc—Gly | 2 |
| 32 | Boc—Val | 2 |
| 31 | Boc—Asn | 2 × 2 |
| 30 | Boc—Thr | 2 |
| 29 | Boc—Pro | 2 |
| 28 | Boc—Val | 2 |

| Amino Acid No. | Protected Amino Acid | Amount Used (mM) |
| --- | --- | --- |
| 27 | Boc—Phe | 2 |
| 26 | Boc—Asn | 2 × 2 |
| 25 | Boc—Asn | 2 × 2 |
| 24 | Boc—Lys(Cl—Z) | 2 |
| 23 | Boc—Val | 2 |
| 22 | Boc—Val | 2 |
| 21 | Boc—Gly | 2 |
| 20 | Boc—Gly | 2 |
| 19 | Boc—Gly(Bzl) | 2 |
| 18 | Boc—Arg(Tos) | 2 × 2 |
| 17 | Boc—Ser(Bzl) | 2 |
| 16 | Boc—Leu | 2 |
| 15 | Boc—Phe | 2 |
| 14 | Boc—Asp(OBzl) | 2 |
| 13 | Boc—Ala | 2 |
| 12 | Boc—Leu | 2 |
| 11 | Boc—Arg(Tos) | 2 × 2 |
| 10 | Boc—His(Tos) | 2 |
| 9 | Boc—Thr(Bzl) | 2 |
| 8 | Boc—Val | 2 |
| 7 | Boc—Cys(MBzl) | 2 |
| 6 | Boc—Thr(Bzl) | 2 |
| 5 | Boc—Ala | 2 |
| 4 | Boc—Thr(Bzl) | 2 |
| 3 | Boc—Asn | 2 × 2 |
| 2 | Boc—Cys(MBzl) | 2 |
| 1 | Boc—Ala | 2 |

EXAMPLE 4

Production of [Asp$^{14}$] h-CGRP(1-37):

Anisole (2 ml), dimethylsulfide (2 ml) and ethanedithiol (0.4 ml) were added to [Asp$^{14}$] h-CGRP(1-37)-MBHA-resin of the formula

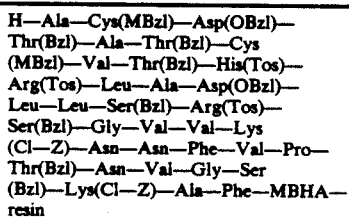

H—Ala—Cys(MBzl)—Asp(OBzl)—
Thr(Bzl)—Ala—Thr(Bzl)—Cys
(MBzl)—Val—Thr(Bzl)—His(Tos)—
Arg(Tos)—Leu—Ala—Asp(OBzl)—
Leu—Leu—Ser(Bzl)—Arg(Tos)—
Ser(Bzl)—Gly—Val—Val—Lys
(Cl—Z)—Asn—Asn—Phe—Val—Pro—
Thr(Bzl)—Asn—Val—Gly—Ser
(Bzl)—Lys(Cl—Z)—Ala—Phe—MBHA—
resin (1.10 g). Anhydrous hydrogen fluoride (20 ml) was added thereto and the mixture was stirred at 0° C. for 1 hour. After the anhydrous hydrogen fluoride was distilled off in vacuo, the residue was washed with ether and 1M acetic acid (20 ml) was added thereto to extract the peptide. The extract was passed through a Dowex WGR (trademark) column (2.5×15 cm) and eluted with 1M acetic acid (150 ml). The eluate was freeze dried to obtain a white powder (390 mg). This powder was dissolved in 50 mM Na$_2$HPO$_4$ buffer (pH 7.5, 20 ml) containing 8M urea and 5 mM dithiothreitol, and stirred for 1 hour, then diluted with 50 mM Na$_2$HPO$_4$ buffer (pH 7.5, 2000 ml), thereafter 20 mM K$_3$Fe(CN)$_6$ aqueous solution (10 ml) was added thereto. The solution was charged on a column of CHP-20P (Mitsubishi Kasei Kogyo trade name) (2.5×24 cm) and was subjected to linear gradient elution with 0.1N aqueous formate (800 ml) containing 5% acetonitrile 0.1N aqueous formate (800 ml) containing 45% acetonitrile. Samples (100 μl) from the fractions (each 10 ml) were measured colorimetrically by the Folin-Lolly method at 750 nm. Fractions Nos. 72-90 were collected and lyophilized to obtain a white powder (160 mg). This powder was charged on a column (2.5×10 cm) of CM-Toyopearl 650M (trademark), and eluted by linear gradient elution with distilled water (600 ml) - 0.4M aq. ammonium acetate (pH 5, 600 ml). Fractions (each 10 ml) Nos. 48-52 were collected and freeze dried to obtain a white powder. The thus-obtained white powder dissolved in 0.1M acetic acid was charged on a column of Sephadex G-25 Fine (trade name) (2.6×90 cm) and eluted with 1M acetic acid. Fractions Nos. 16-30 were collected and lyophilized to obtain a white powder (30 mg). This powder was purified by reverse phase HPLC to obtain purified [Asp$^{14}$] h-CGRP(1-37) (21 mg).

| | |
| --- | --- |
| Column | YMC-GEL ODS S-5 (20 mm ID × 250 mm) |
| Buffer | 0.1% TFA-acetonitrile (a gradient elution with acetonitrile concentration from 29 to 34% for 30 mins.) |
| Flow | 7 ml/min. |
| Fraction | collected at a peak at retention time 18.4 min. |

Physical properties:

$[\alpha]_D^{25}$: −74.74° (C=0.099, 0.1M acetic acid)

Amino acid analysis (6N-HCl hydrolysis):

Asp4.88(5), Thr3.73(4),
Ser2.70(3), Pro1.01(1),
Gly3.05(3), Ala4.00(4),
Val4.63(5), Leu3.05(3),
Phe1.96(2), Lys2.11(2),
His0.98(1), Arg2.03(2),
Cystine0.31(1)

Amino acid analysis (enzymatic hydrolysis by trypsin-amino-peptidase M):

Asp1.86(2), Asn3.22(3),
Thr3.64(4), Ser3.37(3),
Pro1.16(1), Gly3.38(3),
Ala4.00(4), Val5.01(5),
Leu3.32(3), Phe2.19(2),
Lys2.33(2), His1.09(1),
Arg2.15(2), Cystine0.57(1)

Arg is analyzed by citrulline.
The protected amino acids used in the process are as follows:

| Amino Acid No. | Protected Amino Acid | Amount Used (mM) |
| --- | --- | --- |
| 37 | Boc—Phe | 2 |
| 36 | Boc—Ala | 2 |
| 35 | Boc—Lys(Cl—Z) | 2 |
| 34 | Boc—Ser(Bzl) | 2 |
| 33 | Boc—Gly | 2 |
| 32 | Boc—Val | 2 |
| 31 | Boc—Asn | 2 × 2 |
| 30 | Boc—Thr | 2 |
| 29 | Boc—Pro | 2 |
| 28 | Boc—Val | 2 |
| 27 | Boc—Phe | 2 |
| 26 | Boc—Asn | 2 × 2 |
| 25 | Boc—Asn | 2 × 2 |
| 24 | Boc—Lys(Cl—Z) | 2 |
| 23 | Boc—Val | 2 |
| 22 | Boc—Val | 2 |
| 21 | Boc—Gly | 2 |
| 20 | Boc—Gly | 2 |
| 19 | Boc—Ser(Bzl) | 2 |
| 18 | Boc—Arg(Tos) | 2 × 2 |
| 17 | Boc—Ser(Bzl) | 2 |
| 16 | Boc—Leu | 2 |
| 15 | Boc—Leu | 2 |

-continued

| Amino Acid No. | Protected Amino Acid | Amount Used (mM) |
|---|---|---|
| 14 | Boc—Asp(OBzl) | 2 |
| 13 | Boc—Ala | 2 |
| 12 | Boc—Leu | 2 |
| 11 | Boc—Arg(Tos) | 2 × 2 |
| 10 | Boc—His(Tos) | 2 |
| 9 | Boc—Thr(Bzl) | 2 |
| 8 | Boc—Val | 2 |
| 7 | Boc—Cys(MBzl) | 2 |
| 6 | Boc—Thr(Bzl) | 2 |
| 5 | Boc—Ala | 2 |
| 4 | Boc—Thr(Bzl) | 2 |
| 3 | Boc—Asp | 2 × 2 |
| 2 | Boc—Cys(MBzl) | 2 |
| 1 | Boc—Ala | 2 |

EXAMPLE 5

Production of desalanyl-deamino-[Asp$^{14}$] h-CGRP(2-37):

Anisole (2 ml), dimethylsulfide (2 ml) and ethanedithiol (0.4 ml) were added to protected-desalanyl-deamino-[Asp$^{14}$] h-CGRP(2-37)-MBHA-resin of the formula

```
MBzl—S—(CH2)2—CO—Asp(OBzl)—
Thr(Bzl)—Ala—Thr(Bzl)—Cys
(MBzl)—Val—Thr(Bzl)—His(Tos)—
Arg(Tos)—Leu—Ala—Asp(OBzl)—
Leu—Ser(Bzl)—Arg(Tos)—Ser
(Bzl)—Gly—Gly—Val—Val—Lys
(Cl—Z)—Asn—Asn—Phe—Val—Pro—
Thr(Bzl)—Asn—Val—Gly—Ser
(Bzl)—Lys(Cl—Z)—Ala—Phe—MBHA—
resin
```

(1.26 g). Anhydrous hydrogen fluoride (20 ml) was added thereto and the mixture was stirred at 0° C. for 1 hour. After the anhydrous hydrogen fluoride was distilled off in vacuo, the residue was washed with ether and 1M acetic acid (20 ml) was added thereto to extract the peptide. The extract was passed through a Dowex WGR (trademark) column (2.5×15 cm) and eluted with 1M acetic acid (150 ml). The eluate was freeze dried to obtain a white powder (428 mg). This powder was dissolved in 50 mM Na$_2$HPO$_4$ buffer (pH 7.5, 20 ml) containing 8M urea and 5 mM dithiothreitol, and the mixture was stirred at room temperature for 1 hour, then diluted with 50 mM Na$_2$HPO$_4$ buffer (pH 7.5, 2000 ml), thereafter 20 mM K$_3$Fe(CN)$_6$ aqueous solution (12 ml) was added thereto. The solution was charged on a column of CHP-20P (Mitsubishi Kasei Kogyo trade name) (2.5×24 cm) and was subjected to linear gradient elution with 0.1N aqueous formate (800 ml) containing 5% acetonitrile - 0.1N aqueous formate (800 ml) containing 45% acetonitrile. Samples (100 μl) from the fractions (each 10 ml) were measured colorimetrically by the Folin-Lolly method at 750 nm. Fractions Nos. 89-102 were collected and freeze dried to obtain a white powder (116 mg). This powder dissolved in 1M acetic acid was charged on a column (2.6×85 cm) of Sephadex G-25 Fine (trademark), and eluted with 1M acetic acid. Fractions (each 10 ml) Nos. 17-30 were collected and lyophilized to obtain a white powder (54 mg). This powder was purified by reverse phase HPLC as hereinbelow to obtain purified desalanyl-deamino-[Asp$^{14}$] h-CGRP(2-37) (13 mg).

Column: YMC-GEL ODS S-5 AM type (20 mm ID × 250 mm)
Buffer: 0.1% TFA-acetonitrile (a gradient elution with acetonitrile concentration from 31.5 to 32.5% for 30 mins.)
Flow: 7 ml/min.
Fraction: collected at a peak at retention time 19.5 min.

Physical properties:

$[\alpha]_D^{25}$: −81.38° (c=0.091, 0.1M acetic acid)

Amino acid analysis (6N-HCl hydrolysis):

Asp4.78(5), Thr3.69(4),
Ser2.53(3), Pro1.01(1),
Gly2.96(3), Ala3.00(3),
Val4.51(5), Leu2.96(3),
Phe1.95(2), Lys1.98(2),
His0.93(1), Arg1.92(2),

The above protected-desalanyl-deamino [Asp$^{14}$] h-CGRP(2-37)-MBHA-resin was obtained by the following procedure:

Amino acids (sequence from Nos. 3 to 37) were subjected to a coupling reaction by the solid phase synthesis of Example 1 and the peptide was acylated with MBzl-β-mercaptopropionic acid at the final stage of reaction to obtain protected-desalanyl-deamino-[Asp$^{14}$] h-CGRP(2-37)-MBHA-resin.

The protected amino acids used in the process are as follows:

| Amino Acid No. | Protected Amino Acid | Amount Used (mM) |
|---|---|---|
| 37 | Boc—Phe | 2 |
| 36 | Boc—Ala | 2 |
| 35 | Boc—Lys(Cl—Z) | 2 |
| 34 | Boc—Ser(Bzl) | 2 |
| 33 | Boc—Gly | 2 |
| 32 | Boc—Val | 2 |
| 31 | Boc—Asn | 2 × 2 |
| 30 | Boc—Thr | 2 |
| 29 | Boc—Pro | 2 |
| 28 | Boc—Val | 2 |
| 27 | Boc—Phe | 2 |
| 26 | Boc—Asn | 2 × 2 |
| 25 | Boc—Asn | 2 × 2 |
| 24 | Boc—Lys(Cl—Z) | 2 |
| 23 | Boc—Val | 2 |
| 22 | Boc—Val | 2 |
| 21 | Boc—Gly | 2 |
| 20 | Boc—Gly | 2 |
| 19 | Boc—Ser(Bzl) | 2 |
| 18 | Boc—Arg(Tos) | 2 × 2 |
| 17 | Boc—Ser(Bzl) | 2 |
| 16 | Boc—Leu | 2 |
| 15 | Boc—Leu | 2 |
| 14 | Boc—Asp(OBzl) | 2 |
| 13 | Boc—Ala | 2 |
| 12 | Boc—Leu | 2 |
| 11 | Boc—Arg(Tos) | 2 × 2 |
| 10 | Boc—His(Tos) | 2 |
| 9 | Boc—Thr(Bzl) | 2 |
| 8 | Boc—Val | 2 |
| 7 | Boc—Cys(MBzl) | 2 |
| 6 | Boc—Thr(Bzl) | 2 |
| 5 | Boc—Ala | 2 |
| 4 | Boc—Thr(Bzl) | 2 |
| 3 | Boc—Asp | 2 × 2 |
| 2 | MBzl—(CH$_2$)$_2$—COOH | 2 |

What is claimed is:

1. A compound of the formula
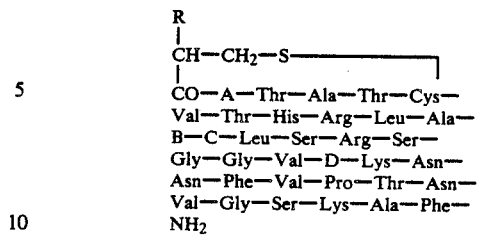
wherein R is H or H—Ala—NH— and when A is Asp, B is Asp or Glu, C is Leu and D is Val: when A is Asn and B is Gly, C is Phe and D is Gly: when A is Asn, B is Asp or Glu and C is Leu, D is Gly: and when A is Asn, B is Asp or Glu, and C is Phe, D is Val, or a pharmaceutically acceptable salt thereof.